United States Patent [19]

Hirose

[11] Patent Number: 4,808,819

[45] Date of Patent: Feb. 28, 1989

[54] MASS SPECTROMETRIC APPARATUS

[75] Inventor: Hiroshi Hirose, Katsuta, Japan

[73] Assignee: Hitachi, Ltd., Tokyo, Japan

[21] Appl. No.: 151,533

[22] Filed: Feb. 2, 1988

[30] Foreign Application Priority Data

Feb. 3, 1987 [JP] Japan .................................. 62-23310

[51] Int. Cl.⁴ .............................................. B01D 59/44
[52] U.S. Cl. ..................................... 250/288; 250/281
[58] Field of Search ........... 250/281, 282, 288, 288 A; 73/23.1

[56] References Cited

U.S. PATENT DOCUMENTS

| 3,626,178 | 12/1971 | Cohen | 250/288 A |
|---|---|---|---|
| 4,105,916 | 8/1978 | Siegel | 250/282 |
| 4,391,778 | 7/1983 | Andresen et al. | 250/288 A |
| 4,509,855 | 4/1985 | Gay | 356/316 |

FOREIGN PATENT DOCUMENTS

| 53-4594 | 1/1978 | Japan . |
|---|---|---|
| 54-14796 | 3/1979 | Japan . |
| 56-78055 | 6/1981 | Japan . |
| 56-152149 | 11/1981 | Japan . |
| 57-837 | 1/1982 | Japan . |
| 57-836 | 1/1982 | Japan . |
| 58-35855 | 3/1983 | Japan . |
| 58-38444 | 3/1983 | Japan . |
| 58-64744 | 4/1983 | Japan . |
| 58-38443 | 5/1983 | Japan . |
| 58-161236 | 9/1983 | Japan . |
| 58-209854 | 12/1983 | Japan . |

OTHER PUBLICATIONS

"Developement of a New Type C/MS Interface and the Applicability for Non Volatile Compounds" M. Zuno et al., Anal. Inst. Tech. and Eng. Div.-Shitsuryo Banseki, vol. 32, No. 3, Aug. 1984, pp. 285-296.

Primary Examiner—Bruce C. Anderson
Attorney, Agent, or Firm—Antonelli, Terry & Wands

[57] ABSTRACT

Separated sample components from a liquid chromatograph and separated sample components from a gas chromatograph are selectively ionized in an LC/MC ion source and a GC/MS ion source, respectively. Ions of sample components obtained by the ionization are focussed into a source slit and the focussed ions are subjected to mass dispersion and detection.

1 Claim, 2 Drawing Sheets

MASS SPECTROMETRIC APPARATUS

BACKGROUND OF THE INVENTION

1. Field of the Invention

This invention relates to a mass spectrometric apparatus and more particularly to a mass spectrometric apparatus suitable for the mass spectrometry of separated sample components in effluents from a gas chromatograph and a liquid chromatograph.

2. Prior Art

A mass spectrometric apparatus for the mass spectrometry of separated sample components in an effluent from a liquid chromatographic column is disclosed in Shitsuryo Bunseki (mass spectroanalysis), Vol. 32, No. 3, pages 285-296, August (1984), where the separated sample components in an effluent from a liquid chromatographic column are sprayed from a nozzle under the back pressure; the sprayed sample components are subjected to solvent removal and then led to an ion source, where the sample components are formed into ions by a chemical ionization with a solvent as a reactang gas, that is, by a solvent-induced chemical ionization; the formed ions are withdrawn from the ion source into a direction perpendicular to the inflow direction of sample components to the ion source, led to a mass spectrometric apparatus and subjected to mass spectrometry. In such a type of mass spectrometric apparatus, there are examples of using a gas chromatograph in place of the liquid chromatography.

SUMMARY OF THE INVENTION

An object of the present invention is to provide a mass spectrometric apparatus suitable for selected mass spectrometry of separated sample components in an effluent from a liquid chromatograph and separated sample components in an effluent from a gas chromatograph.

Another object of the present invention is to provide a mass spectrometric apparatus suitable for selected mass spectrometry of separated sample components in an effluent from a liquid chromatograph and separated sample components in an effluent from a gas chromatograph without changing the liquid chromatograph to the gas chromatograph or vice versa.

According to the present invention, there is provided a mass spectrometric apparatus, which comprises a liquid chromatograph, a first ion source for ionizing separated sample components from the liquid chromatograph, a gas chromatograph, a second ion source for ionizing separated sample components from the gas chromatograph, a means for selectively actuating the first and second ion sources, thereby selectively forming ions of the separated sample components from the liquid chromatograph in the first ion source and ions of the separated sample components from the gas chromatograph in the second ion source, a means for focussing the ions selectively formed in the first and second ion sources onto a predetermined position, a means for mass dispersing the focussed ions and a means for detecting the mass dispersed ions.

PREFERRED EMBODIMENTS OF THE INVENTION

Figure 1:
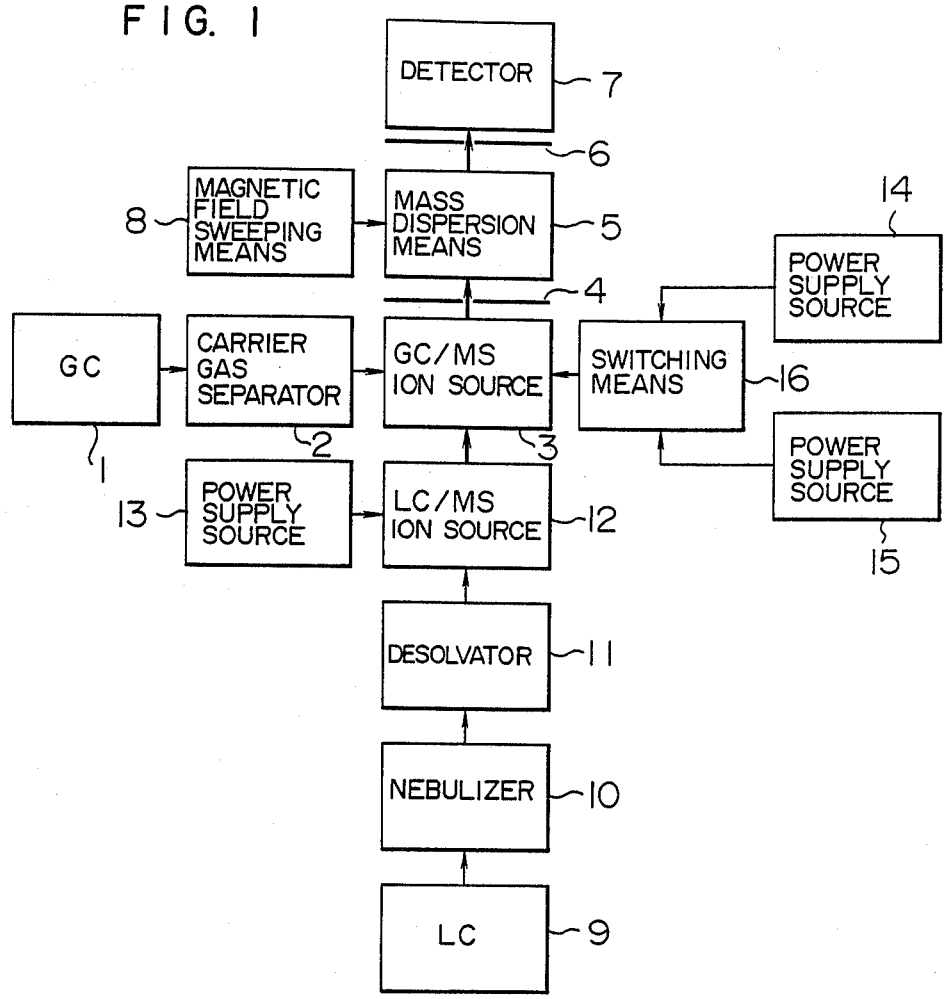
FIG. 1 is a block diagram for a mass spectrometric apparatus according to one embodiment of the present invention.

In a gas chromatograph mode (GC mode) in FIG. 1, an effluent gas composed of a carrier gas and separated sample components from a gas chromatograph (GC) 1 is led to a carrier gas separator 2, which may be of a well known Beeman type or of a jet type, where the carrier gas in the effluent gas is removed from the separated sample components. The separated sample components are then led to a GC/MS ion source 3 and ionized by electron bombardment. The thus formed ions in an ion beam form are focussed into a source slit 4, and the ion beam that has passed through the source slit 4 is led to a mass dispersion means 5, which comprises an electromegnet, and the thus led ions are dispersed according to their mass numbers by the magnetic field generated by the electromagnet. Among the dispersed ions, ions having specific mass numbers are focussed into a collector slit 6, passed therethrough and detected by a detector 7. By sweeping the magnetic field with a magnetic field sweeping means 8, ions having various mass numbers are successively detected by the detector 7. This is the so called mass number sweeping. The detector 7 emits electric signals which are proportional to the quantities (numbers) of ions having various mass numbers, successively detected by the detector 7, and the electric signals are recorded on a recorder (not shown in the drawing) to record the mass spectra or are input into a data processor (not shown in the drawing) and memorized.

In a liquid chromatograph mode (LC mode), an effluent composed of an eluting solution and separated sample components from a liquid chromatograph (LC) 9 is led to a nebulizer 10 which makes the effluent from LC into a jet mist stream. The jet mists are composed of combinations of solute molecules, i.e. molecules of separated sample components, and solvent molecules. The jet mist stream is then heated in a desolvator 11 and subjected to solvent removal.

Generally, the solute molecules are weak against heat, but most of the heat applied thereto is consumed as the heat of vaporization of the solvent and thus excessive heating of the solute molecules can be avoided. The nebulizer 10 and the desolvator 11 themselves are well known.

The solute molecules from the desolveator 11, that is, the molecules of the separated sample components, are led to an LC/MS ion source 12 to form ions. The thus formed ions pass through the GC/MS ion source 3 and focussed into the source slit 4. The ion beam that has passed through the source slit 4 is subjected to the mass number sweeping in the same manner as in the case of GC mode. Output signals from the detector 7 are led to the recorder or once led to the data processor and memorized in the same manner as in the case of GC mode.

A power supply source 13 is directed to the LC/MS ion source 12, and is on in the case of LC mode and off in the case of GC mode. Power supply sources 14 and 15 are selectively connected to the GC/MS ion source 3 by a switching means 16. That is, in the case of GC mode the power supply source 14 is connected to the GC/MS ion source 3 and in the case of LC mode the power supply source 15 is connected to the GC/MS ion source 3.

Figure 2:
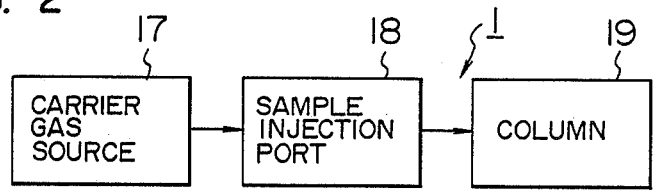
FIG. 2 is a block diagram of the gas chromatograph in FIG. 1.

In FIG. 2, GC 1 comprises a carrier gas source 17, a sample injection port 18 and a column 19. Carrier gas is led to the column 19 from the carrier gas source 17, whereas a sample is injected into the column 19 through the sample injection port 18. Thus, the sample passes through the column 19 while being carried with the carrier gas. The column 19 may be a packed column in which a filler is packed, or a capillary column which comprises a capillary and an adsorbent formed on the inside surface, or of any other type, if available. The sample undergoes separation owing to a difference in the affinity toward the filler or adsorbent while being passed through the column 19. Gas chromatograph is well known, and more detailed description of it will be omitted.

Figure 3:
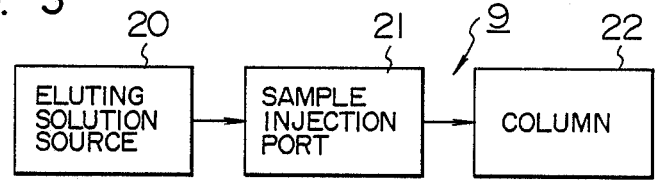
FIG. 3 is a block diagram of the liquid chromatograph in FIG. 1.

In FIG. 3, GC 9 comprises an eluting solution source 20, a sample injection port 21 and a column 22. An eluting solution is led to the column 22 from the eluting solution source 20, whereas a sample is injected into the column 22 through the sample injection port 21. Thus, the sample is passed through the column 22 while being carried by the eluting solution. The column 22 usually comprises a tube and a filler packed therein, and the sample undergoes separation owing to a difference in the affinity towards the filler while being passed through the column 22. The liquid chromatograph is also well known and more detailed description of it will be omitted.

Figure 4:
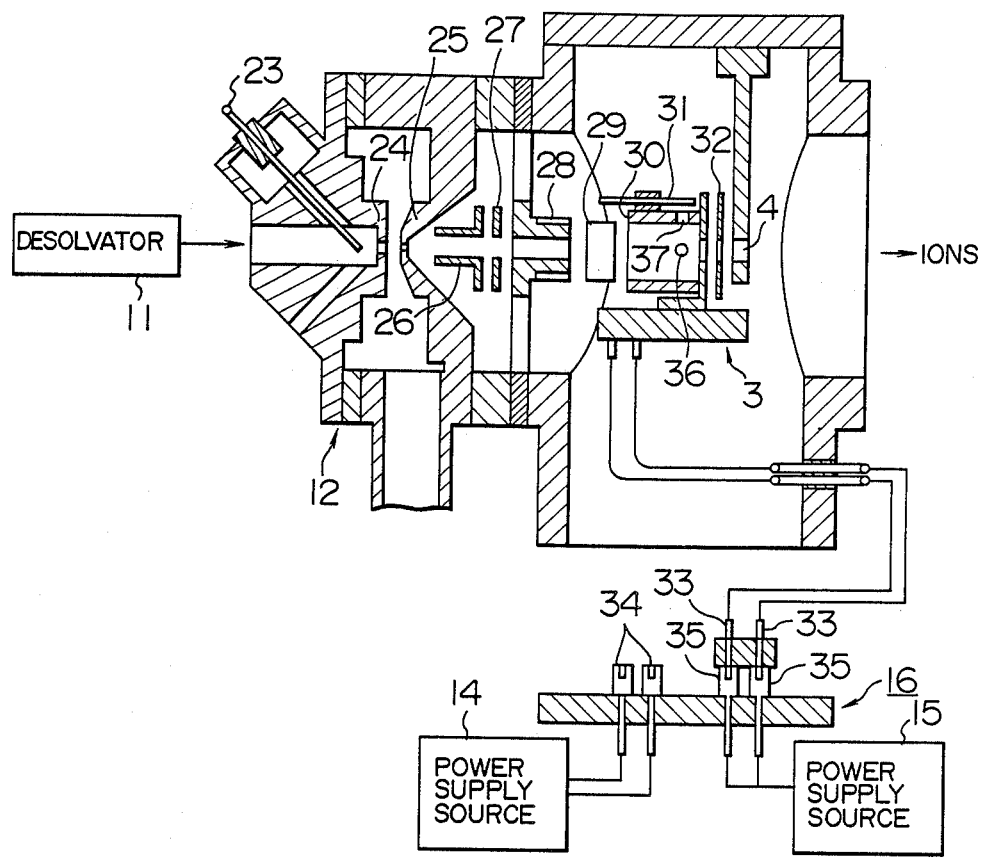
FIG. 4 is a cross-sectional view of one embodiment of LC/MS ion source and GC/MS ion source in FIG. 1.

In FIG. 4, in the case of LC mode, the separated sample components from the desolvator 11 are led to the space between a needle electrode 23 and a first pore electrode 24 of LC/MS ion source 12. A corona discharge takes place between the electrode, whereby ionization of solvent molecules existing together with sample molecules is carried out. Successively, these ions undergo ion-molecule reaction with solute molecules, whereby the solute molecules are ionized. The ionization can be regarded as a chemical ionization under the atmospheric pressure, using the solvent molecuels as a reagent, and when the proton affinity of solute molecules is higher than that of solvent molecules, proton addition ionization takes place.

The thus formed ions are withdrawn by a withdrawal electrode 26 through the first pore electrode 24 and a second pore electrode 25, subjected to lens action under a potential between a lens electrode 27 and a lens base electrode 28 and focussed into the source slit 4 under an earth potential.

As described above, the corona discharge and ion-molecule reaction take place under the atmospheric pressure, and thus the pressure applied to the tip end of the needle electrode 23 is one atmosphere. The pressure prevailing between the first pore electrode 24 and the second pore electrode 25 is 0.2 Torr and the pressure prevailing at the ion withdrawal electrode 26 and thereafter is $10^{-5}$ to $10^{-6}$ Torr.

Typically, the potential of the needle electrode 23 is 6 kV, the corona discharge current is 5 $\mu$A, the potential of the first pore electrode 24 is 3.05 to 3.1 kV, the potential of the second pore electrode 25 is 3 kV, the potential of the ion withdrawal electrode 26 is the earth potential, the potential of the lens electrode 27 is 2.5 to 2.8 kV, and the potential of the lens base electrode 28 is the earth potential. The potential between the first pore electrode 24 and the second pore electrode 25 (50–100 V) is called drift potential, and splitting of ions can be adjusted between these two pore electrodes by adjusting the drift potential.

The source slit 4 is long in the parallel direction with the surface of the drawing and narrow in the direction perpendicular to the surface of the drawing, which corresponds to the mass dispersion direction of ions by the mass dispersion means 5.

A polarization electrode device 29 comprises a pair of electrodes arranged in parallel with each other in the direction perpendicular to the surface of the drawing, and a positive potential is applied to one of the electrodes from the power supply source 15 and a negative potential is applied to other electrode from the power supply source 15, whereby ions passing through the space between a pair of the electrodes are polarized into the direction perpendicular to the surface of the drawing so as to efficiently pass through the source slit 4.

Ionization chamber 30, filament 31 and lens electrode 32 of the GC/MS ion source 3 are maintained at the earth potential in the case of LC mode. A potential may be applied to the lens electrode 32 from the power supply source 15 so that the ions can be focussed into the source slit 4.

In the case of GC mode, the power supply source 13 is turned off, whereby the LC/MS ion source 12 is inactivated. In the case of GC mode, the power supply source 14 is connected to the GC/MS ion source 3 in place of the power supply source 15. The connection switching is carried out by the switching means 16.

In the case of FIG. 4, the switching means 16 is of a mechanical type and comprises male electric contactors 33 and female electric contactors 34 and 35 into which the male electric contactors 33 are screwed. The female electric contactors 34 and 35 are connected to the power supply sources 14 and 15, respectively. By selectively screwing the male electric contactor 33 with the female electric contactors 34 or 35, the power supply source 34 or 35 can be selectively connected to the GC/MS ion source 3. When the power supply source 14 is connected to the GC/MS ion source 3 by the switching means 16, the ionization chamber 30 is maintained at 3 kV, the filament 31 at 3.02 kV, and the lens electrode 32 at 28 kV. A repeller potential (variable between 0 and 10 V) is applied to a pair of the electrodes of the polarization electrode device 29.

In the case of GC mode, the separated sample gas components from the carrier gas separator 2 are led to the ionization chamber 36 through a gas injection port 36. The thus injected sample gas components are ionized by bombardment of thermal electrons which are generated at the filament 31 and led to the ionization chamber 30 through an electron path port 37. Ions of the ionized sample gas components are pushed out under the repeller potential and focussed into the source slit 4 by the lens electrode 32. The ions that have passed through the source slit 4 are subjected to mass dispersion by the mass dispersion means 5 in the same manner as in the case of LC mode. Among the dispersed ions, those ions having a specific mass number are focussed into the collector slit 6 and the ions that have passed through the collector slit 6 are detected by the detector 7. Mass number sweeping is attained by sweeping the magnetic field generated by the mass dispersion means 5 through the magnetic field sweeping means 8 in the same manner as in the case of LC mode. Output signals from the detector 7 are led to the recorder or once led to the data processor and memorized in the same manner as in the case of LC mode.

It is obvious from the foregoing description that the separated sample components in an effluent from a liquid chromatograph and the separated sample components in an effluent from a gas chromatograph can be selectively subjected to mass spectrometry without troublesome exchange between the liquid chromatograph and the gas chromatograph.

In the case of GC mode, the LC/MS ion source 12 is in an inactivated state and thus is exposed to substantially the atmospheric pressure, whereas the GC/MS ion source 3 is in a vacuum state. Thus, air flows in the GC/MS ion source 3. The air inflow has an adverse effect upon the mass spectrometric performance in GC mode. Thus, it is desirable to prevent air inflow into the GC/MS ion source 3 from the LC/MS ion source 12 in GC mode.

Figure 5:
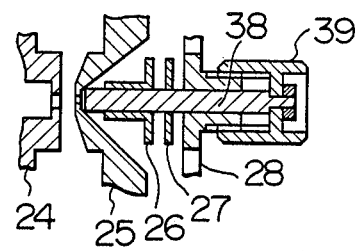
FIG. 5 is a vertical cross-sectional view of one embodiment of a gas block valve suitable for the practice of the embodiment of FIG. 1.

In FIG. 5, a rod value 38 is provided through the lens base electrode 28, the lens electrode 27 and the ion withdrawal electrode 26, and a cap nut 39 is provided at the head of the valve 38. By screwing the cap nut 39 into the male screw on the lens base electrode 28, the tip end of the valve 38 is brought into tight contact with the second pore electrode 25 to close the pore in the electrode 25, whereby the air inflow into the GC/MS ion source 3 from the LC/MS ion source 12 can be prevented.

The mechanical switching means 16 in FIG. 4 may be replaced with an electronic one.

It is pointed out that these embodiments merely illustrate the principle of the invention only by way of example and many other modifications and variations are conceivable without departing from the spirit and scope of the invention.

What is claimed is:

1. A mass spectrometric apparatus, which comprises a liquid chromatograph, a first ion source for ionizing separated sample components from the liquid chromatograph, a gas chromatograph, a second ion source for ionizing separated sample components from the gas chromatograph, a means for selectively actuating the first and second ion sources, thereby selectively forming ions of the separated sample components from the liquid chromatograph in the first ion source and ions of the separated sample components from the gas chromatograph in the second ion source, a means for focussing the ions selectively formed in the first and second ion sources onto a predetermined position, a means for mass dispersing the focussed ions and a means for detecting the mass dispersed ions.

* * * * *